US008889611B2

(12) United States Patent  
Reinhardt et al.

(10) Patent No.: US 8,889,611 B2
(45) Date of Patent: Nov. 18, 2014

(54) BLEACH CATALYST COMPOUNDS, METHOD FOR THE PRODUCTION THEREOF AND USE THEREOF

(75) Inventors: Gerd Reinhardt, Kelkheim (DE); Michael Best, Bad Soden (DE)

(73) Assignee: Clariant International Ltd, Muttene (CH)

( * ) Notice: Subject to any disclaimer, the term of this patent is extended or adjusted under 35 U.S.C. 154(b) by 141 days.

(21) Appl. No.: 13/513,729

(22) PCT Filed: Nov. 30, 2010

(86) PCT No.: PCT/EP2010/007235
§ 371 (c)(1),
(2), (4) Date: Aug. 14, 2012

(87) PCT Pub. No.: WO2011/066935
PCT Pub. Date: Jun. 9, 2011

(65) Prior Publication Data
US 2012/0302490 A1 Nov. 29, 2012

(30) Foreign Application Priority Data

Dec. 5, 2009 (DE) .......................... 10 2009 057 222

(51) Int. Cl.
| | | |
|---|---|---|
| C11D 7/26 | (2006.01) | |
| C11D 7/32 | (2006.01) | |
| C11D 7/54 | (2006.01) | |
| C07F 13/00 | (2006.01) | |
| C11D 17/06 | (2006.01) | |
| C11D 17/00 | (2006.01) | |
| C11D 3/16 | (2006.01) | |
| C11D 3/39 | (2006.01) | |
| D21C 9/10 | (2006.01) | |
| D21C 9/16 | (2006.01) | |

(52) U.S. Cl.
CPC ............ C07F 13/005 (2013.01); C11D 17/065 (2013.01); C11D 17/0052 (2013.01); C11D 17/06 (2013.01); C11D 3/168 (2013.01); C11D 3/3932 (2013.01); D21C 9/10 (2013.01); D21C 9/163 (2013.01)
USPC ........... 510/311; 510/349; 510/357; 510/375; 510/499; 510/500; 510/441; 510/445; 510/446

(58) Field of Classification Search
CPC ............ C11D 1/22; C11D 3/28; C11D 3/392; C11D 3/3932; C11D 17/0052; C11D 17/06; C11D 17/065; B01J 23/34; B01J 27/24
USPC ......... 510/311, 349, 357, 375, 499, 500, 441, 510/445, 446; 502/200, 324
See application file for complete search history.

(56) References Cited

U.S. PATENT DOCUMENTS

| | | | |
|---|---|---|---|
| 4,444,674 A * | 4/1984 | Gray ............................ | 510/313 |
| 5,114,611 A * | 5/1992 | Van Kralingen et al. ....................... | 252/186.33 |
| 5,194,416 A * | 3/1993 | Jureller et al. ................ | 502/167 |
| 5,274,147 A | 12/1993 | Kerschner et al. | |
| 5,429,769 A * | 7/1995 | Nicholson et al. ............ | 510/376 |
| 5,516,738 A | 5/1996 | Jureller et al. | |
| 6,365,564 B1 * | 4/2002 | Kott et al. ..................... | 510/376 |
| 6,395,703 B2 * | 5/2002 | Scepanski ..................... | 510/445 |
| 2001/0025695 A1 | 10/2001 | Patt et al. | |
| 2001/0044402 A1 | 11/2001 | Dai et al. | |
| 2002/0066542 A1 | 6/2002 | Jakob et al. | |
| 2003/0207784 A1 * | 11/2003 | Himmrich et al. ............. | 510/441 |
| 2005/0209120 A1 | 9/2005 | Reinhardt et al. | |
| 2009/0126121 A1 | 5/2009 | de Almeida et al. | |
| 2010/0024846 A1 | 2/2010 | Warkotsch et al. | |
| 2010/0029536 A1 | 2/2010 | Warkotsch et al. | |
| 2010/0031976 A1 | 2/2010 | Warkotsch et al. | |

FOREIGN PATENT DOCUMENTS

| | | | |
|---|---|---|---|
| DE | 102007006627 A1 | 8/2008 | |
| DE | 102007006630 A1 | 8/2008 | |
| DE | 102007044417 A1 | 3/2009 | |
| EP | 0458397 A2 | 11/1991 | |
| EP | 0458398 A2 | 11/1991 | |
| EP | 0530870 A1 | 3/1993 | |
| EP | 1557457 A1 | 7/2005 | |
| EP | 1621605 A1 | 2/2006 | |
| JP | 2002212596 A | 7/2002 | |

(Continued)

Primary Examiner — Gregory R Delcotto
(74) Attorney, Agent, or Firm — Michael W. Ferrell

(57) ABSTRACT

The invention relates to compounds in solid form, containing a) one or more manganese complex compounds of the general formula (1), where M is independently selected from manganese in the III or IV oxidation state, X is independently a co-ordinating or bridging species selected from $H_2O$, $O_2^{2-}$, $O_2^{-}$, $O^{2-}$, $OH^{-}$, $HO_2^{-}$, $SH^{-}$, $S^{2-}$, $SO$, $Cl^{-}$, $N^{3-}$, $SCN^{-}$, $N_3^{-}$, $RCOO^{-}$, $NH_2^{-}$ and $NR_3$, where R is a radical selected from H, alkyl and aryl, L are independently organic ligands, each of which contains at least two nitrogen atoms co-ordinated on manganese, z is an integer from −4 to +4, Y is a monovalent or multivalent counter-ion selected from chloride, sulphate, hydrogen sulphate, nitrate and acetate, which leads to charge neutrality of the complex, and q is an integer from 1 to 4, and b) one or more salts of the general formula $R'-C_6H_4-SO_3Me$, where R' is $CH_3$ or $C_2H_5$ and denotes Me, Na, K, Ca or Mg, characterized in that the molar ratio of the manganese complex compound of the general formula (1) to salt of the general formula $R'-C_6H_4-SO_3Me$ is 1:0.5 to 1:5. The invention also describes a method for producing the compounds and to the use thereof as oxidation catalysts or bleach catalysts, in particular in detergents or cleaning agents.

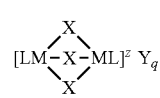

(1)

20 Claims, No Drawings

(56) References Cited

FOREIGN PATENT DOCUMENTS

| | | |
|---|---|---|
| JP | 2005206835 A | 8/2005 |
| WO | 9606154 A1 | 2/1996 |
| WO | 0042151 A1 | 7/2000 |
| WO | 02088063 A1 | 11/2002 |
| WO | 2006125517 A1 | 11/2006 |
| WO | 2008086937 A2 | 7/2008 |
| WO | 2008095554 A2 | 8/2008 |

* cited by examiner

BLEACH CATALYST COMPOUNDS, METHOD FOR THE PRODUCTION THEREOF AND USE THEREOF

The invention relates to bleach catalyst compounds comprising per se hygroscopic bleach catalysts and organic carrier materials, in particular salts of short-chain alkylbenzenesulfonic acids having fewer than 3 carbon atoms in the alkyl chain, to methods for the production thereof and to the use thereof as oxidation or bleach catalysts, in particular in detergents or cleaners.

In European powder detergents, the bleach component has for a long time been based on bleaches which release peroxide compounds during washing. These highly oxidative compounds very effectively remove a very wide variety of stain types, such as, for example, from tea, wine and fruits. Depending on the peroxide compound used, mostly perborates or percarbonates, the washing temperatures required for effective bleaching are between 60 and 95° C. At temperatures below 60° C., by contrast, the effectiveness of the oxygen bleach drops considerably. For economic and ecological reasons, endeavors are therefore being made to find compounds which permit an oxygen bleaching even at low temperatures. Whereas for the purposes of improving the bleaching performance of detergents on textile fabrics at low temperatures, mostly bleach activators such as tetraacetylethylenediamine (TAED), nonanoyloxybenzene-sulfonate-sodium (NOBS) or decanoyloxybenzoic acid (DOBA) have caught on, for the purposes of cleaning hard surfaces, e.g. in dishwashing detergents, bleach catalysts are increasingly being used alongside bleach activators. Here, a good cleaning performance on stubborn tea stains in particular is expected. More recently, bleach catalysts have also been used to a greater extent in textile and paper bleaching and also in chemical synthesis (oxidation reactions).

These bleach catalysts are mostly metal-containing compounds of iron, cobalt or manganese. On the one hand, relatively simple compounds such as metal salts (e.g. manganese acetates) or coordination compounds such as cobalt pentamineacetates are used, on the other hand transition metal complexes with open-chain or cyclic ligands are of particular interest since they surpass the bleaching performance of the simple systems many times over. From the series of the last-mentioned catalysts, in particular manganese or iron complexes comprising ligands based on triazacyclononane and derivatives thereof have particular bleaching-active effectiveness or high oxidation power.

Examples of production and use of such metal complexes are described inter alia in US 2009/0126121, WO 2008/086937, US 2002/0066542, US 2001/0044402, US 2001/0025695, U.S. Pat. No. 5,516,738, WO 2002/088063 and EP 0 530 870. For their simple handling during production, processing and use, it is in many cases necessary to use solid, low hygroscopicity compounds. Here, bleach catalysts and oxidation catalysts which comprise large-volume counterions such as hexafluorophosphate, perchlorate or tetraphenylborate in particular have proven useful. Such complexes are described e.g. in EP 0 458 397, EP 0 458 398 and WO 96/06154.

Large-volume counterions such as hexafluorophosphate, perchlorate or tetrafluoroborate anions lead to crystalline metal complexes which precipitate out of the reaction mixture and can therefore be isolated easily. They are not hygroscopic and can therefore be readily incorporated into detergents and cleaners, where they are characterized by good storage stability. However, perchlorate salts are potentially explosive, which largely restricts their use in consumer products.

By contrast, hexafluorophosphates are in most cases sparingly water-soluble, which has an adverse effect on their performance in some areas of application.

U.S. Pat. No. 5,274,147 discloses that small counterions such as chloride, sulfate or acetate anions lead to oily products. These are strongly hygroscopic and are therefore preferably used in the form of aqueous solutions, as described e.g. in WO 2006/125517.

An advantage of the last-mentioned catalysts is their very good solubility in water and also their simple industrial synthesis. A disadvantage of using them in pulverulent or tableted detergents and cleaners is their strong hygroscopicity and, resulting therefrom, their poor handability in powder form, which leads to lumps. Associated therewith is a poor physical storage stability in solid or pulverulent applications.

There is therefore a need for readily water-soluble non-hygroscopic or low hygroscopicity transition metal complexes based on manganese, and for methods for the production thereof which can be carried out on an industrial scale.

Surprisingly, it has now been found that specific, per se hygroscopic manganese complexes with organic ligands, in particular based on polyazacycloalkanes such as e.g. triazacyclononane, and small counterions such as e.g. chloride, sulfate and acetate, can be converted to non-hygroscopic or only low-hygroscopicity compounds by bringing them into contact with, such as, for example, mixing with or applying to, salt(s) of short-chain alkylbenzenesulfonic acids, where the alkyl chain consists of fewer than three carbon atoms.

Within the context of the present invention, "compounds" are understood as meaning compositions that are solid at room temperature (25° C.), such as e.g. solid mixtures. These are present for example in the form of powders or granules.

The present invention therefore provides compositions, preferably physical mixtures, in solid form comprising a) one or more manganese complex compounds of the formula (1)

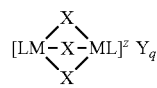

in which

M independently of the others is selected from manganese in oxidation state III or IV, X independently of the others is a coordinating or bridging species selected from $H_2O$, $O_2^{2-}$, $O_2^-$, $O^{2-}$, $OH^-$, $HO_2^-$, $SH^-$, $S^{2-}$, $SO$, $Cl^-$, $N^{3-}$, $SCN^-$, $N_3^-$, $RCOO^-$, $NH_2^-$, and $NR_3$, where R is a radical selected from H, alkyl, preferably $C_1$-$C_4$-alkyl, and aryl, preferably phenyl, L independently of the others is organic ligands which each contain at least two nitrogen atoms coordinated to manganese, z is an integer from −4 to +4, Y is a monovalent or multivalent counterion selected from chloride, sulfate, hydrogen sulfate, nitrate and acetate (OAc), which leads to the charge neutrality of the complex, and q is an integer from 1 to 4, and b) one or more salts of the formula R'—$C_6H_4$—$SO_3$Me, in which R' is $CH_3$ or $C_2H_5$ and Me is Na, K, Ca or Mg, wherein the molar ratio of manganese complex compound of the formula (1) to a salt of the formula R'—$C_6H_4$—$SO_3$Me is from 1:0.5 to 1:5, preferably from 1:1 to 1:2.

The compositions according to the invention are only slightly hygroscopic, if at all, and are characterized inter alia by an advantageous storage stability. They are present in solid form at room temperature.

The organic ligand L is preferably one which is an at least nine-membered ring in which at least two, preferably three or four, nitrogen atoms are involved in the ring and coordinate with the manganese. Examples which may be mentioned are: 1,4,7-triazacyclononane (TACN), 1,4,7-trimethyl-1,4,7-triazacyclononane (1,4,7-Me$_3$-TACN), 1,5,9-triazacyclododecane (TACD), 1,5,9-trimethyl-1,5,9-triazacyclododecane (1,5,9-Me$_4$-TACD), 1,4,7,10-tetraazacyclododecane (cyclam), 1,4,7,10-tetramethyl-1,4,7,10-tetraazacyclododecane (1,4,7,10-Me$_4$-cyclam), 2-methyl-1,4,7-trimethyl-1,4,7-triazacyclononane (2-Me-1,4,7-Me$_3$-TACN), 2-methyl-1,4,7-triazacyclononane (2-Me-TACN) or 1,2-bis(4,7-dimethyl-1,4,7-triazacyclonon-1-yl)ethane (Me$_4$-DTNE). From this group, particular preference is given to 1,4,7-trimethyl-1,4,7-triazacyclononane (1,4,7-Me$_3$-TACN) and 1,2-bis-(4,7-dimethyl-1,4,7-triazacyclonon-1-yl)ethane (Me$_4$-DTNE). 1,4,7-Trimethyl-1,4,7-triazacyclononane (1,4,7-Me$_3$-TACN) is especially preferred.

Particularly preferred manganese complex compounds of the formula (1) are

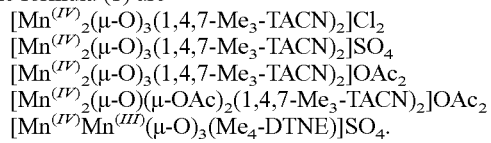

[Mn$^{(IV)}_2$(μ-O)$_3$(1,4,7-Me$_3$-TACN)$_2$]Cl$_2$
[Mn$^{(IV)}_2$(μ-O)$_3$(1,4,7-Me$_3$-TACN)$_2$]SO$_4$
[Mn$^{(IV)}_2$(μ-O)$_3$(1,4,7-Me$_3$-TACN)$_2$]OAc$_2$
[Mn$^{(IV)}_2$(μ-O)(μ-OAc)$_2$(1,4,7-Me$_3$-TACN)$_2$]OAc$_2$
[Mn$^{(IV)}$Mn$^{(III)}$(μ-O)$_3$(Me$_4$-DTNE)]SO$_4$.

Among these compounds, preference is in turn given to [Mn$^{(IV)}_2$(μ-O)$_3$ (1,4,7-Me$_3$-TACN)$_2$] Cl$_2$ (tri-μ-oxobis[(1,4,7-trimethyl-1,4,7-triazacyclo-nonane)manganese(IV)] dichloride) and [Mn$^{(IV)}_2$(μ-O)$_3$ (1,4,7-Me$_3$-TACN)$_2$]SO$_4$ (tri-μ-oxobis[(1,4,7-trimethyl-1,4,7-triazacyclononane) manganese(IV)]sulfate).

The synthesis of the manganese complex compounds of the formula (1) takes place in a manner known per se, e.g. as described in WO 2006/125517. In a preferred embodiment, the reaction of a divalent manganese salt with the ligand L takes place in water as solvent to form a coordination compound of the manganese(II) salt and the ligand L, then the manganese(II) coordination compound formed is oxidized with an oxidizing agent while simultaneously maintaining a pH of at least 11 and preferably at least 12, for converting the manganese from the divalent state to the trivalent and/or tetravalent state. By subsequently adding an organic or inorganic acid, the pH is adjusted to a value ≤9.0. Any manganese oxides or hydroxides formed are separated off by filtration.

In this method, a water-soluble manganese(II) salt, preferably from the group of the acetates, chlorides, nitrates and sulfates, for example manganese diacetate, manganese dichloride, manganese sulfate or manganese nitrate, is reacted with a ligand compound L, preferably in the molar ratio of from 4:1 to 1:2, particularly preferably in the molar ratio of from 2:1 to 1:1 and especially preferably in the molar ratio of from 1.5:1 to 1:1.

The reaction of the manganese(II) salt with the ligand L is carried out in water as the sole solvent. Only enough water is used for at least 15 parts by weight of manganese(II) salt plus ligand compound to be present per 100 parts per weight of water. The upper limit of the concentration of manganese(II) salt and ligand compound can be very high because this and the further reactions can be carried out either in solution or in suspension (dispersion). The upper concentration limit is thus essentially given by the stirrability of the reaction mixtures. The manganese(II) salt and the ligand are accordingly used together in an amount of from preferably 15 to 500 parts by weight, particularly preferably 20 to 200 parts by weight, per 100 parts by weight of water. The reaction of the manganese (II) salt with the ligand L in water is carried out preferably at a temperature of from 10 to 30° C., particularly preferably 15 to 25° C. (room temperature), and atmospheric pressure. This step leads to the formation of a coordination compound of the manganese(II) salt and the ligand compound dissolved in the solvent mixture.

The manganese(II) coordination compound is then oxidized at a pH of from 11 to 14, preferably 12 to 13, the oxidizing agent and the base preferably being introduced simultaneously to establish the stated pH. The oxidation is carried out preferably by simultaneous mixing in of an oxidizing agent from the group air, pure oxygen, hydrogen peroxide, alkali metal peroxide and alkali metal permanganate and an alkali metal hydroxide into the solution obtained in step a) while maintaining the stated pH. Preferably, the oxidation is carried out by mixing in a (prepared) mixture consisting of a 0.5 to 35% strength by weight, preferably 3 to 20% strength by weight, aqueous hydrogen peroxide solution and a 5 to 40% strength by weight, preferably 10 to 30% strength by weight, aqueous alkali metal (sodium or potassium) hydroxide solution. As far as the temperature and the pressure are concerned, the oxidation is preferably carried out at 3 to 15° C., particularly preferably 5 to 10° C., and atmospheric pressure. Here, the divalent manganese used is oxidized to the trivalent or to the preferred tetravalent state.

The reaction mixture is then adjusted to pH 5 to 9, preferably pH 6 to 8, by adding an organic or inorganic acid, such as acetic acid, sulfuric acid or hydrochloric acid.

The resulting manganese complex compounds of the formula (1) can then be isolated by removing the water.

A particularly preferred alkylbenzenesulfonic acid which forms the basis of the one or more salts of the formula R'—C$_6$H$_4$—SO$_3$Me, in which R' is CH$_3$ or C$_2$H$_5$ and Me is Na, K, Ca or Mg, is toluenesulfonic acid. By contrast, mixtures of such manganese complexes with relatively long-chain alkylbenzenesulfonates, but also with relatively long-chain alkylsulfonates or with relatively long-chain alkylsulfates, where "relatively long-chain alkyl" is in particular alkyl having more than 2 carbon atoms, have proven to be unsuitable for industrial use since they are hygroscopic and have a tendency towards caking during production and processing and have an inadequate storage stability.

In a preferred embodiment of the invention, the compositions according to the invention comprise a salt of the formula R'—C$_6$H$_4$—SO$_3$Me, in which R' is CH$_3$ and Me is Na.

In a further preferred embodiment of the invention, the compositions according to the invention have a total amount of the one or more manganese complex compounds of the formula (1) and the one or more salts of the formula R'—C$_6$H$_4$—SO$_3$Me, in which R' is CH$_3$ or C$_2$H$_5$ and Me is Na, K, Ca or Mg, of ≥70.0% by weight, preferably of ≥75.0% by weight, particularly preferably of ≥77.0% by weight and especially preferably of ≥78.0% by weight. The upper limit for the total amounts just given can be 100% by weight and is preferably 99.9% by weight. Further preferred upper limits for the total amounts just given are 98.9% by weight or 89.9% by weight, particularly when the compositions according to the invention comprise further constituents such as e.g. inorganic salts.

In a further preferred embodiment of the invention, the compositions according to the invention comprise one or more inorganic salts. If the compositions according to the invention comprise one or more inorganic salts, these are preferably present in the compositions according to the invention in an amount of from 1 to 25% by weight and particularly preferably in an amount of from 10 to 20% by weight. Among the inorganic salts, sodium chloride and sodium sulfate are preferred.

In a further preferred embodiment of the invention, the compositions according to the invention have a total amount of the one or more manganese complex compounds of the formula (1), the one or more salts of the formula $R'—C_6H_4—SO_3Me$, in which R' is $CH_3$ or $C_2H_5$ and Me is Na, K, Ca or Mg, and the one or more inorganic salts optionally present in the composition of ≥95.0% by weight, particularly preferably of ≥97.0% by weight and especially preferably of ≥98.0% by weight. The upper limit for the total amounts just given can be 100% by weight. A preferred upper limit for the total amounts just given is 99.9% by weight. If the compositions according to the invention comprise no inorganic salts, the total amounts just given refer to the sum of the amounts of the one or more manganese complex compounds of the formula (1) and of the one or more salts of the formula $R'—C_6H_4—SO_3Me$, in which R' is $CH_3$ or $C_2H_5$ and Me is Na, K, Ca or Mg. If, however, the compositions according to the invention comprise one or more inorganic salts, the total amounts just given refer to the sum of the amounts of the one or more manganese complex compounds of the formula (1), of the one or more salts of the formula $R'—C_6H_4—SO_3Me$, in which R' is $CH_3$ or $C_2H_5$ and Me is Na, K, Ca or Mg, and of the one or more inorganic salts.

Preferably, the compositions according to the invention comprise water in an amount ≤5.0% by weight. The compositions according to the invention particularly preferably comprise water in an amount ≤3.0% by weight and especially preferably in an amount ≤2.0% by weight. The compositions according to the invention can be anhydrous. A preferred lower limit for the amounts of water just given is 0.1% by weight.

In a further preferred embodiment of the invention, the compositions according to the invention consist of the one or more manganese complex compounds of the formula (1), the one or more salts of the formula $R'—C_6H_4—SO_3Me$, in which R' is $CH_3$ or $C_2H_5$ and Me is Na, K, Ca or Mg, and also optionally one or more inorganic salts and optionally water in the small amounts stated above.

In a particularly preferred embodiment of the invention, the compositions according to the invention consist of the one or more manganese complex compounds of the formula (1), the one or more salts of the formula $R'—C_6H_4—SO_3Me$, in which R' is $CH_3$ or $C_2H_5$ and Me is Na, K, Ca or Mg, and water in the small amounts stated above.

In a further particularly preferred embodiment of the invention, the compositions according to the invention consist of the one or more manganese complex compounds of the formula (1), the one or more salts of the formula $R'—C_6H_4—SO_3Me$, in which R' is $CH_3$ or $C_2H_5$ and Me is Na, K, Ca or Mg, one or more inorganic salts and water in the small amounts stated above.

In a further preferred embodiment of the invention, the compositions according to the invention are present in the form of a powder or granules. In a particularly preferred embodiment of the invention, they are present in the form of granules. In a particularly preferred embodiment of the invention, the granules according to the invention are coated with a coating layer.

The aforementioned total amounts of the one or more manganese complex compounds of the formula (1) and the one or more salts of the formula $R'—C_6H_4—SO_3Me$, in which R' is $CH_3$ or $C_2H_5$ and Me is Na, K, Ca or Mg, and also the aforementioned total amounts of the one or more manganese complex compounds of the formula (1) and the one or more salts of the formula $R'—C_6H_4—SO_3Me$, in which R' is $CH_3$ or $C_2H_5$ and Me is Na, K, Ca or Mg, and the one or more inorganic salts optionally additionally present in the compositions according to the invention (and also the aforementioned amounts for the inorganic salts on their own) refer e.g. to compositions according to the invention in non-granulated form. However, they can also refer to compositions according to the invention in granulated form if they have been produced without granulation auxiliaries such as, for example, binders. If, however, granulation auxiliaries have been used for the granulation, the stated amounts refer to the total amount of the compositions according to the invention minus these granulation auxiliaries. In the same way, any coating materials used for the coating of granules should be taken into consideration. The aforementioned amounts of water, by contrast, refer to all compositions according to the invention, i.e. for example also to granules produced with the help of granulation auxiliaries and to coated granules.

The present invention also further provides a method for producing the compositions according to the invention.

The resulting manganese complex compounds of the formula (1) can, for example after producing them and obtaining them in water, be isolated by removing the water and, with the exclusion of moisture and/or water in solid form, be brought into contact with solid alkylbenzenesulfonates of the formula $R'—C_6H_4—SO_3Me$, in which R' is $CH_3$ or $C_2H_5$ and Me is Na, K, Ca or Mg, by intimate mixing.

Preferably, however, an aqueous solution of the manganese complex compounds of the formula (1) is brought into contact with an alkylbenzene-sulfonate of the formula $R'—C_6H_4—SO_3Me$, in which R' is $CH_3$ or $C_2H_5$ and Me is Na, K, Ca or Mg. Particular preference is given here to sodium toluenesulfonate. This bringing into contact can take place in various ways.

In a preferred embodiment of the method according to the invention, alkylbenzenesulfonate, which is solid or dissolved or slurried in water, of the formula $R'—C_6H_4—SO_3Me$, in which R' is $CH_3$ or $C_2H_5$ and Me is Na, K, Ca or Mg, is added to dissolve the manganese complex compound of the formula (1), and the mixture is then converted to a solid form by removing water. This can take place by means of standard evaporation or by spray-drying.

In a particularly preferred embodiment of the method according to the invention, an aqueous solution of the manganese complex compound of the formula (1) is mixed with a 30 to 80% strength by weight aqueous solution or slurry of the alkylbenzenesulfonates of the formula $R'—C_6H_4—SO_3Me$, in which R' is $CH_3$ or $C_2H_5$ and Me is Na, K, Ca or Mg, at 5 to 100° C., preferably at 15 to 50° C., where the molar ratio of manganese complex compound of the formula (1) to alkylbenzenesulfonate is from 1:1 to 1:2. The mixture can then be dried by removing the water.

In a further particularly preferred embodiment of the method according to the invention, the dissolved manganese complex compounds of the formula (1) are homogeneously mixed with an aqueous solution or slurry of the alkylbenzenesulfonates of the formula $R'—C_6H_4—SO_3Me$, in which R' is $CH_3$ or $C_2H_5$ and Me is Na, K, Ca or Mg, and subjected to a spray-drying, the gas outlet temperature being in the range from 100° C. to 150° C. The pulverulent solid (compound) according to the invention obtained in this way is characterized by a low hygroscopicity and can be further processed without further safety precautions (moisture exclusion).

In a further particularly preferred embodiment of the method according to the invention, an aqueous mixture of manganese complex compound of the formula (1) and alkylbenzenesulfonate of the formula $R'—C_6H_4—SO_3Me$, in which R' is $CH_3$ or $C_2H_5$ and Me is Na, K, Ca or Mg, is homogeneously mixed with an aqueous solution or dispersion of an inorganic salt, for example $Na_2SO_4$, and subjected to a spray-drying, the gas outlet temperature being in the range from 100° C. to 150° C.

The method according to the invention described above and the thereby effected generation of a composition according to the invention achieves a significant reduction in the hygroscopicity and thus a considerable improvement in the storage stability of the otherwise strongly hygroscopic manganese complex compounds of the formula (1).

In order to further improve the storage stability of the compositions according to the invention, it is advantageous to use the compositions according to the invention in granulated form.

The compositions according to the invention can, for example, be compressed with or without the addition of a binder, compacted and comminuted gently to granule sizes of from 200 to 2000 μm.

Also suitable is a build-up granulation in a mixer, for example in a plowshare mixer, annular bed mixer or intensive mixer with the addition of a binder, in particular an anhydrous binding system, for example a fatty alcohol polyglycol ether or a polyglycol ether such as PEG 6000.

Furthermore, pulverulent compositions according to the invention can be subjected, with or without the addition of a binder, to a shaping granulation through dies in an extruder, but also by means of edge-runner presses, edge runners, optionally with downstream spheronizer. In the same way, the dried solid substance of the above-described precipitation reaction or the dry powder obtained by spray-drying can be granulated.

Furthermore, an aqueous solution or a slurry of the compositions according to the invention can be converted to particle form (granules) by fluidized-bed granulation.

To further increase the storage stability, it is advantageous to coat the granules of the compositions according to the invention with coating substances.

Suitable coating materials are all film-forming substances, preferably waxes, silicones, fatty acids, soaps, anionic surfactants, nonionic surfactants, cationic surfactants, and anionic and cationic polymers, e.g. polyacrylic acids. The use of these coating materials can, inter alia, delay the dissolution behavior in order, in this way, to also prevent interactions between the bleach activator and an enzyme system, which may be present for example in a detergent formulation, at the start of the washing process. If the granules according to directions are to be used in machine dishwashing detergents, waxes with melting points of from 40 to 50° C. are primarily suitable for this purpose.

Acidic coating materials increase the storage stability of the granules in percarbonate-containing, highly alkaline formulations and suppress color damage by spotting. Additions of a dye are likewise possible.

The coating materials are generally applied by spraying on the molten coating materials or coating materials dissolved in a solvent. The coating material is applied to the granule core preferably in amounts of from 0.1 to 20% by weight and particularly preferably in amounts of from 1 to 10% by weight, based on the total weight of the coated granules.

In an especially preferred embodiment of the method according to the invention, the one or more salts of the formula R'—$C_6H_4$—$SO_3Me$, in which R' is $CH_3$ or $C_2H_5$ and Me is Na, K, Ca or Mg, are added to an aqueous solution or dispersion comprising the one or more manganese complex compounds of the formula (1) and optionally additionally one or more inorganic salts, all of the constituents are mixed and then dried, and if the composition is present as optionally coated granules, a granulation step and optionally a coating step follow.

The compositions according to the invention are characterized by a good storage stability in pulverent detergents, cleaners and disinfectant formulations. They are ideal for use in heavy-duty detergents, stain removal salts, machine dishwashing detergents, pulverulent all-purpose cleaners and denture cleaners.

The compositions according to the invention, e.g. in the form of granules, can, as oxidation catalysts, be used in particular as bleach component in detergents and cleaners in the home or in commercial laundries, as well as in the bleaching of textiles and paper and also in industrial oxidation reactions.

The compositions according to the invention are only slightly hygroscopic, if at all, have good storage stability and are characterized by their better solubility in water compared to hexafluorophosphate complexes. They are therefore suitable in particular for use in pulverulent or tableted products such as machine dishwashing detergents, where they are used in combination with a peroxide source such as hydrogen peroxide, percarbonate or perborates in aqueous applications.

The present invention therefore also further provides the use of a composition according to the invention as oxidation or bleach catalyst, in particular in detergents or cleaners.

The invention is illustrated in more detail below by reference to examples and comparative examples, although these are not to be understood as being limiting.

COMPARATIVE EXAMPLE 1

39.6 g of manganese dichloride-4-hydrate (0.2 mol) are charged in 110 g of water to a 1 liter flask and admixed with 34.3 g of 1,4,7-trimethyl-1,4,7-triazacyclononane (0.2 mol). The solution is cooled and admixed with a mixture of 60.3 g (0.301 mol) of 20% strength by weight sodium hydroxide solution and 226.7 g (0.2 mol) of 3% strength by weight hydrogen peroxide solution at 10 to 15° C. When the addition is complete, the reaction mixture (pH>12.5) is adjusted to a pH of 6 with aqueous hydrochloric acid. The solids (manganese oxides/hydroxides) of the reaction mixture are filtered off with suction and the resulting filtrate is completely reduced by evaporation. The solids (manganese oxides/hydroxides) of the reaction mixture are filtered off with suction and the resulting filtrate is completely reduced by evaporation. The red-brown residue is dissolved in ethanol and the insoluble constituents (e.g. sodium chloride) are separated off. Complete evaporation of the solvent produces 56.2 g (95%) of tri-μ-oxobis[(1,4,7-trimethyl-1,4,7-triazacyclononane)-manganese(IV)]dichloride as a strongly hygroscopic, red-brown powder.

Upon storage in an open dish, the product absorbs >17% by weight of water at room temperature over the course of 24 hours and becomes liquid.

EXAMPLE 1

Tri-μ-oxobis[(1,4,7-trimethyl-1,4,7-triazacyclononane) manganese(IV)]dichloride is prepared analogously to comparative example 1 and isolated in pure form as a red-brown powder. 4.7 g (8 mmol) thereof are dissolved in 50 ml of water and admixed with 3.1 g (16 mmol) of toluene-4-sulfonic acid sodium salt (Merck). After-stirring is carried out for 1 hour at room temperature, followed by evaporation to dryness on a rotary evaporator. This gives 7.8 g of a crystalline violet solid which, after storage for 14 days at 38° C. and a relative atmospheric humidity of 70%, has absorbed 1.8% by weight of water and remains free-flowing at the same time.

EXAMPLE 2

Analogously to comparative example 1, an aqueous solution of 0.2 mol of tri-µ-oxobis[(1,4,7-trimethyl-1,4,7-triaza-cyclononane)manganese(IV)]dichloride in water is prepared and freed from manganese oxides/hydroxides. The salts contained as a result of the reaction (sodium chloride) remain in the solution. At 25° C., 0.4 mol (77.6 g) of solid toluene-4-sulfonic acid sodium salt (Merck) is added and the mixture is after-stirred for 30 minutes. The clear dark red solution is then evaporated to dryness. Drying in a vacuum drying cabinet gives a crystalline red-violet solid in 92.7% yield, a mixture of tri-µ-oxobis[(1,4,7-trimethyl-1,4,7-triaza-cyclononane)manganese(IV)]dichloride, sodium toluenesulfonate and sodium chloride. Upon open storage, this product absorbs ca. 2% by weight of water over the course of 5 days, remains crystalline and free-flowing.

COMPARATIVE EXAMPLE 2

The procedure is in accordance with example 2 but adding sodium cumenesulfonate instead of the sodium toluene-4-sulfonate (equimolar exchange of sodium toluene-4-sulfonate for sodium cumenesulfonate). Evaporation at 50° C. gives a red-brown solid which, after 5 days, absorbs 7.1% by weight of water and in so doing becomes lumpy.

COMPARATIVE EXAMPLE 3

4.4 g (7.5 mmol) of isolated tri-µ-oxobis[(1,4,7-trimethyl-1,4,7-triazacyclo-nonane)manganese(IV)]dichloride according to comparative example 1 are dissolved in 50 ml of water, and 4.3 g (15 mmol) of sodium dodecylsulfate are added. The mixture is after-stirred for 1 hour at room temperature and then evaporated to dryness on a rotary evaporator. This gives 8.7 g of crystalline red solid which, after storage for 5 days at room temperature, absorbs 8.7% by weight of water and in so doing becomes lumpy.

The invention claimed is:
1. A composition in solid form comprising
a) at least one manganese complex compounds of the formula (1)

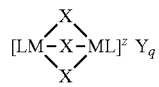
(1)

wherein
M independently of the others is selected from the group consisting of manganese in oxidation state III and IV,
X independently of the others is a coordinating or bridging species selected from the group consisting of $H_2O$, $O_2^{2-}$, $O_2^{2-}$, $O^{2-}$, $OH^-$, $HO_2^-$, $SH^-$, $S^{2-}$, $SO$, $Cl^-$, $N^{3-}$, $SCN^-$, $N_3^-$, $RCOO^-$, $NH_2^-$, and $NR_3$, where R is a radical selected from the group consisting of H, alkyl and aryl,
L independently of the others is an organic ligand which each contain at least two nitrogen atoms coordinated to manganese,
z is an integer from −4 to +4,
Y is a monovalent or multivalent counterion selected from the group consisting of chloride, sulfate, hydrogen sulfate, nitrate and acetate, which leads to the charge neutrality of the complex, and
q is an integer from 1 to 4, and
b) at least one salt of the formula R'—$C_6H_4$—$SO_3$Me, in which R' is $CH_3$ or $C_2H_5$ and Me is Na, K, Ca or Mg, wherein the molar ratio of manganese complex compound of the formula (1) to a salt of the formula R'—$C_6H_4$—$SO_3$Me is from 1:0.5 to 1:5.

2. The composition as claimed in claim 1, wherein L in the at least one manganese complex compound of the formula (1) is an organic ligand which is an at least nine-membered ring in which at least two, nitrogen atoms are involved in the ring and coordinate with the manganese.

3. The composition as claimed in claim 1, wherein L in the at least one manganese complex compound of the formula (1) is selected from the group consisting of 1,4,7-trimethyl-1,4,7-triazacyclononane and 1,2-bis(4,7-dimethyl-1,4,7-triazacyclonon-1-yl)ethane.

4. The composition as claimed in claim 1, wherein the at least one manganese complex compound of the formula (I) is selected from the group consisting of:
[$Mn^{(IV)}_2(\mu-O)_3(1,4,7-Me_3-TACN)_2$]$Cl_2$,
[$Mn^{(IV)}_2(\mu-O)_3(1,4,7-Me_3-TACN)_2$]$SO_4$,
[$Mn^{(IV)}_2(\mu-O)_3(1,4,7-Me_3-TACN)_2$]$OAc_2$,
[$Mn^{(IV)}_2(\mu-O)(\mu-OAc)_2(1,4,7-Me_3-TACN)_2$]$OAc_2$, and
[$Mn^{(IV)}Mn^{(III)}(\mu-O)_3(Me_4-DTNE)$]$SO_4$.

5. The composition as claimed in claim 1, wherein R' is $CH_3$ and Me is Na.

6. The composition as claimed in claim 1, wherein the content of the at least one manganese complex compound of the formula (1) and the at least one salt of the formula R'—$C_6H_4$—$SO_3$Me, is ≥70.0% by weight.

7. The composition as claimed in claim 1, further comprising at least one inorganic salt.

8. The composition as claimed in claim 1, further comprising water in an amount of ≤5.0% by weight.

9. The composition as claimed in claim 1, in the form of granules.

10. The granules as claimed in claim 9, wherein the granules are coated.

11. A method for producing a composition as claimed in claim 1, comprising the steps of adding the at least one salt of the formula R'—$C_6H_4$—$SO_3$Me, in which R' is $CH_3$ or $C_2H_5$ and Me is Na, K, Ca or Mg, to an aqueous solution or dispersion comprising the at least one manganese complex compound of the formula (1) and optionally, at least one inorganic salt, mixing all of these constituents and subsequently drying the mixture.

12. An oxidation or bleach catalyst, comprising a composition as claimed in claim 1.

13. The composition as claimed in claim 1, wherein L in the at least one manganese complex compound of the formula (1) is an organic ligand which is an at least nine-membered ring in which three or four nitrogen atoms are involved in the ring and coordinate with the manganese.

14. A detergent or cleaner comprising the oxidation or bleach catalyst as claimed in claim 12.

15. The method as claimed in claim 11, further comprising the step of granulating the dry mixture.

16. The method as claimed in claim 15, further comprising the step of coating the granulated dry mixture.

17. The composition as claimed in claim 1, wherein the at least one manganese complex compound of the formula (I) is selected from the group consisting of:
(tri-µ-oxobis[(1,4,7-trimethyl-1,4,7-triazacyclononane) manganese(IV)]dichloride); and
(tri-µ-oxobis[(1,4,7-trimethyl-1,4,7-triazacyclononane) manganese(IV)]sulfate).

18. The composition as claimed in claim 1, wherein the composition is produced by intimate mixing or wet-mixing an aqueous solution of the manganese complex compound of the formula (1) with the alkylbenzenesulfonates of the formula R'—$C_6H_4$—$SO_3$Me, in which R' is $CH_3$ or $C_2H_5$ and Me is Na, K, Ca or Mg.

19. The composition as claimed in claim 1, wherein the composition is produced by a process comprising the steps of adding the at least one salt of the formula R'—$C_6H_4$—$SO_3$Me, in which R' is $CH_3$ or $C_2H_5$ and Me is Na, K, Ca or Mg, to an aqueous solution or dispersion comprising said at least one manganese complex compound and optionally, at least one inorganic salt, mixing all of these constituents and subsequently drying the mixture.

20. A composition in solid form comprising:
  a) at least one manganese complex compound selected from the group consisting of:
    $[Mn^{(IV)}_2(\mu\text{-}O)_3(1,4,7\text{-}Me_3\text{-}TACN)_2]Cl_2$,
    $[Mn^{(IV)}_2(\mu\text{-}O)_3(1,4,7\text{-}Me_3\text{-}TACN)_2]SO_4$,
    $[Mn^{(IV)}_2(\mu\text{-}O)_3(1,4,7\text{-}Me_3\text{-}TACN)_2]OAc_2$,
    $[Mn^{(IV)}_2(\mu\text{-}O)(\mu\text{-}OAc)_2(1,4,7\text{-}Me_3\text{-}TACN)_2]OAc_2$, and
    $[Mn^{(IV)}Mn^{(III)}(\mu\text{-}O)_3(Me_4\text{-}DTNE)]SO_4$ and
  b) at least one salt of the formula R'—$C_6H_4$—$SO_3$Me, in which R' is $CH_3$ or $C_2H_5$ and Me is Na, K, Ca or Mg,
  wherein the molar ratio of manganese complex compound to the salt of the formula R'—$C_6H_4$—$SO_3$Me is from 1:0.5 to 1:5 and wherein the composition is produced by a process comprising the steps of adding the at least one salt of the formula R'—$C_6H_4$—$SO_3$Me, in which R' is $CH_3$ or $C_2H_5$ and Me is Na, K, Ca or Mg, to an aqueous solution or dispersion comprising said at least one manganese complex compound and optionally, at least one inorganic salt, mixing all of these constituents and subsequently drying the mixture.

* * * * *